| # | 3,949,086 |
|---|---|
| | Apr. 6, 1976 |

United States
Wolfson

[54] ANTIFUNGAL OR ANTIBACTERIAL COMPOSITION AND METHOD

[75] Inventor: Leonard L. Wolfson, Milwaukee, Wis.

[73] Assignee: Nalco Chemical Company, Chicago, Ill.

[22] Filed: Nov. 2, 1970

[21] Appl. No.: 86,366

Related U.S. Application Data

[63] Continuation-in-part of Ser. No. 454,986, May 11, 1965, abandoned, and a continuation-in-part of Ser. No. 770,785, Oct. 25, 1968, abandoned.

[52] U.S. Cl................ 424/302; 106/15 R; 162/161
[51] Int. Cl.$^2$............................................. A01N 9/18
[58] Field of Search ....................................... 424/302

[56] References Cited
UNITED STATES PATENTS

| | | | |
|---|---|---|---|
| 1,511,762 | 10/1924 | Hutzelman | 424/334 |
| 1,879,351 | 9/1932 | Lehmann et al. | 424/346 |
| 2,188,944 | 2/1940 | Fox et al. | 424/346 |
| 2,246,524 | 6/1941 | Kyrides | 424/325 X |
| 2,549,358 | 4/1951 | Bacon et al. | 424/346 |
| 3,062,710 | 11/1962 | Moyle et al. | 424/346 |
| 3,067,095 | 12/1962 | Baltazzi | 424/246 |
| 3,073,691 | 1/1963 | Bluestone | 424/275 |
| 3,252,855 | 5/1966 | Wehner | 424/302 |
| 3,275,505 | 9/1966 | Herschler | 424/317 |

*Primary Examiner*—Dale R. Ore
*Attorney, Agent, or Firm*—Henry L. Brinks

[57] ABSTRACT

The biocide, methylenebisthiocyanate, may be combined with 2,4,5-trichlorophenol to provide a synergistically effective antifungal and antibacterial composition.

10 Claims, No Drawings

ANTIFUNGAL OR ANTIBACTERIAL COMPOSITION AND METHOD

This application is a continuation-in-part of my earlier filed Ser. No. 454,986, filed May 11, 1965, now abandoned, and a continuation-in-part of my earlier filed Ser. No. 770,785, filed Oct. 25, 1968, now abandoned.

The invention relates to the control of microorganisms present in aqueous fluid media through the use of certain novel combinations of microbiocides. More particularly, the present invention is concerned with a method of inhibition and control of microorganisms in industrial process water systems through the use of combinations of methylenebisthiocyanate and certain other classes of materals.

The inhibition and control of the growth and reproduction of microorganisms in aqueous recirculating waters in industrial processes has long been recognized as a particularly burdensome problem. The environment of the aqueous medium itself is often extremely conducive to rapid multiplication and growth of these undesirable microorganisms. Only through the use of carefully tailored microbiocidal compositions can the growth and reproduction of these undesirable organisms be controlled reliably without detriment to the process in which the water is used. Without effective control, loss of product, inferior product, production-time loss, and other types of expensive problems may occur in the system.

The particular problems inherent in the microbiological control of an aqueous fluid medium are vastly different than those involving control of other harmful organisms in environmental conditions other than that of water. For example, many times a chemical is rendered completely inactive by the particular surrounding media containing the undesirable microorganisms. Compounds such as ethylene oxide and betapropiolactone which are well-known fungicides, are completely or nearly completely inactive in aqueous media with regard to inhibition of growth and reproduction of the microorganisms contained therein.

General considerations of antimicrobic agents and processes reveal that efficient control of each specific type of microorganism growth, requires a specific chemical-physical type of treatment. The choice of the active chemical composition and/or the method of application depends upon the system to be controlled. Different biocidal processes and antibiotic chemicals cannot legitimately be equated in a general manner.

Many broad classes of biocidal agents are known to the art. It is also known that antiseptics, nematocides disinfectants, fumigants, fungistats, fungicides, preservatives, chemical and physical sterilants, and pasteurization agents must all be particularly designed to obviate the specific problem at hand. The inherent chemical make-up of each class of composition intrinsically depends upon the organisms to be conrolled and medium in which they are contained. Physical form, in addition to chemical configuration, may also be important. For example, in the control of insects, the particular chemical normally must be low boiling and capable of volatilization in order to contact the undesirable pest. In like manner a fumigant must have a high degree of toxicity to insects in all states of their life cycle.

One problem in the broad spectrum of microbiological control is that of industrial process water systems. This is the problem solved by the instant invention. In order to economically utilize the aqueous industrial process media, it is often necessary to recirculate it in a continuous manner over long periods of time. This recirculation causes many difficult problems, among which is the gradual build-up and accumulation of undesirable microorganisms in the aqueous fluid. Various species of bacteria and fungi are favorably produced in such an environment of recirculating use.

One of the most acute industrial biological control problems is that in papermill water systems which contain aqueous dispersions of paper-making fibers. The uncontrolled build-up of microbiological slime due to the accumulation of microorganisms, causes off-grade production, increased maintenance costs, decreased production because of breaks, and the requirement of more frequent wash-ups and excessive raw usage. For example, slime deposits result in contamination of the stock by deposition thereon with consequent breaks in the subsequently formed sheets. It has been discovered that chemical control of these microorganisms will obviate the problems recited above. Application of selected slimicides to strategic locations throughout the paper-making process, achieves good control and does away with potentially troublesome conditions.

In the paper mill industry itself the widespread adoption of closed white water systems creates especially severe operating conditions since this system lends itself to accumulation of slime deposits by virtue of the continuous recycling of the white water. In order to overcome the problems created by the presence of slime in these closed white water systems, paper manufacturers have for a long time been seeking slime control agents which not only keep slime in abeyance by inhibiting its growth, but also effect a kill and inhibit initial slime formation by impairment of a vital function of slime-forming organisms, namely, reproduction.

A typical closed white water paper-making process may generally be thought to include the following steps:

1. Stock preparation;
2. Formation of a wet web by filtration and vacuum, and;
3. Removal of the water from the formed web or sheet by pressing and heat.

The various pulps such as unbleached groundwood, unbleached sulphite, bleached sulphite, unbleached kraft and Mitscherlich, semi-bleached kraft, etc., prepared by well-known processes, are then subjected to the desired mechanical treatment, generally known as stock preparation. This step includes processing such as slushing, beating and refining. Slushing or dispersing the fibers in water may be done in such machines as a Hydrapulper. The stock suspension is later subjected to beating and refining, that is, cutting processes to increase fiber surface and flexibility, and decrease fiber lengths. A typical refining operation is carried out in a Jordan Conical Refiner.

The second general process step of arrangement of the fibers in suspension into a wet web is normally effected by a Fourdrinier or cylinder machine. In general, a Fourdrinier machine is preferred and will be described below. This step consists of flowing the dilute suspension of fibers evenly on a surface of a continuous belt or wire cloth. The water of the web is removed by gravity, suction, and pressure. However, before the stock suspension is formed on the wire cloth it is placed in a machine chest to provide the necessary reserve needed for machine operation to regulate the flow. The suspension of fibrous material is transported from the machine chest to the headbox, the latter converting the flow into a flat stream and then to a slice wire which controls the stream and therefore the sheet thickness.

The water leaving the wire of the Fourdrinier machine is commonly known as white water and is caught on trays underneath the machine. In order to recover fibers and other solids from this white water it is necessary to employ a so-called Saveall type of recovery. This may include such processes as filtration and sedimentation. An example of a flotation process involves the use of a Sveen Saveall. Here, white water is treated with a chemical such as glue whereby the fibers are caused to adhere to each other and are subsequently skimmed off the surface of the water.

The complexity of the above system coupled with favorable growth conditions for microorganisms through the use of recirculating water causes slime masses to thrive and form throughout the various individual parts of the system. Particularly troublesome areas are corners of equipment, areas of poor stock flow, and high density storage sites. These slime masses prevent normal flow of stock suspension, make the stock lumpy, and prevent normal sheet formation.

Generally, paper mill systems contain from 0.1% to 15% by weight of cellulosic fiber material in the form of an aqueous pulp. Such an aqueous pulp medium is potentially conducive to the growth of such bacteria as *Pseudomonas aeruginosa*, *Aerobacter aerogenes*, *Bacillus mycoides*, *Desulfovibrio*, *desulfuricans*, *Clostridia*, and fungi such as *Pencillium glaucum*, *Cephalosporium*, *Aspergillus terreus*, *Trichoderma* and *Aspergillus niger*.

Another use of water in industry is that of an efficient cooling medium for industrial cooling towers, air conditioning equipment, internal combustion engines, and the like.

Since heat may be easily and economically removed by water in such systems as evaporative cooling towers, these systems have been widely adopted in many industries. Again, the water used in such systems is recirculated, thus complicating the problem of microbiological control. Slime build-ups also result in large adherent masses which plug equipment and restrict flow. These same microorganisms cause deterioration of cooling tower lumber by selective removal of cellulose from the surface. It has been found that even small amounts of nutrients found in cooling tower systems support these microorganisms in their reproduction and defeat control efforts. Solution of this specialized and difficult industrial problem not only requires use of effective chemicals to control microorganisms, but in addition these same chemicals must possess a sufficiently high vapor pressure so as not to be carried off and create a potential hazard to those working in the area.

One approach to the problem of control of microorganisms in industrial process waters has been effected through the use of methylenebisthiocyanate. However, use of relatively large amounts of this material are necessary, which, when taken in conjunction with its high chemical cost makes its use somewhat disadvantageous. It would be an advance in the art if combinations of methylenebisthiocyanate and other chemical classes would be discovered which possess synergistic activity, whereby only extremely small amounts of the former chemical need be used to give effective microbiological control of industrial process waters.

It, therefore, becomes an object of this invention to provide a class of microbiocidal agents stable in aqueous media which are effective in controlling the microorganisms contained in industrial process water systems.

Another object of the invention is to provide an effective method of inhibition and control of growth and reproduction of undesirable microorganisms contained in a myriad of differently constituted aqueous fluid media.

Still another object is to provide combinations of chemicals which will inhibit and control microorganisms in industrial process water systems in a synergistic manner, and which will cause little toxicity hazard to the operator of such systems.

A specific object is the control of papermill slime deposits through the use of synergistic blends of methylenebisthiocyanate and a variety of other specific chemical classes, and particularly to provide a method of microbiocidal inhibition useful in such specific papermill systems as a closed white water system.

Yet another object is the protection of cooling tower systems from build-up of microorganisms which may undesirably produce loss of heat exchange capcity, by use of the above blends of compositions which do not tend to escape from the treated system.

Other objects will appear hereinafter.

In accordance with the invention a blend of materials has been discovered which exhibits biocidal synergism when used to control and inhibit the growth and reproduction of microorganisms in industrial process waters. Specifically, it has been found that combinations of methylenebisthiocyanate and certain other classes of materials synergistically act as microbiological control agents when such combinations are incorporated with industrial process waters.

Specifically, it has been discovered that methylenebisthiocyanate may be combined with 2,4,5-trichlorophenol to produce biologically active compositions which are extremely useful in treating a variety of industrial process waters.

The 2,4,5-trichlorophenol may be employed in the form of its alkali metal salts where such is desirable from a standpoint of formulation and use suitability.

Methylenebisthiocyanate may be combined with 2,4,5-trichlorophenol to afford synergistic microbiological compositions. The methylenebisthiocyanate to biologically active chemical ratio is generally defined as 1:01 to 1:20. A preferred ratio range of methylenebisthiocyanate to 2,4,5-trichlorophenol is 1:0.5 to 1:10.

As will be shown later by experimental evidence, certain combinations of methylenebisthiocyanate with 2,4,5-trichlorophenol is most effective when used in certain specific proportions. To generally indicate some of the more preferred blends which may be used in the practice of the invention, Table I is set forth below:

Table I

| Weight Ratio of methylenebisthiocyanate to Active Agents | | |
|---|---|---|
| III. | Methylenebisthiocyanate: | 2,4,5-trichlorophenol |
| | General range | 1:0.1 to 1:20 |
| | Preferred | 1:0.5 to 1:10 |

By treating industrial process waters with one or more of the above-described combinations of chemical materials, the invention is also directed to provide a microbiologically controlled industrial process water which comprises a major portion of an aqueous liquid and a minor portion of at least a microbiocidal reactive amount of the methylenebisthiocyanate combination material. Excellent microbiological control of such treated waters is present even for long periods of time and under conditions of recirculation.

The method of inhibition of growth and reproduction of microbiological organisms in industrial process water systems broadly comprises the step of treating the system by adding thereto at least a microbiocidal amount of the synergistic blend of methylenebisthiocyanate and one or more of the additional classes of chemicals outlined above. The total amount of synergistic composition required to achieve control of microorganisms will, of course, vary, depending upon the particular system treated, as well as the types of species found present. In most cases, as little as 0.05 ppm to about 25 ppm of combination treatment will give adequate control, although quantities ranging from about 0.1 ppm as high as 100 ppm may be necessary in some cases. Small additive quantities of the composition of the invention are extremely effective in industrial process systems where the water is recirculated and re-used. In these systems quantities of the chemical will gradually build up to a maximum usable and effective treating dosage, which may be calculated knowing the specific factors in each particular system.

The invention is particularly useful when the combination of chemical treating agents is added to paper-making systems and industrial cooling water systems. A water system which can be treated with particular success by the above process is a closed white water system. Moreover, slime-producing organisms in any paper-making process water system may be generally inhibited by the use of the compositions of the invention. Particularly, however, excellent biostat activity is shown in inhibiting growth and reproduction of *Flavobacterium brevis*, *Aerobacter aerogenes*, *Desulfovibrio desulfuricans*, *Clostridia* and *Aspergillus niger*.

It has been determined that when the chemicals of the invention are used in paper mill systems and particularly in closed white water paper mill systems, the amount of chemical used in effectively controlling the microorganisms contained therein may, vary from 0.01 to 10 pounds per ton of paper pulp. More preferably, the chemical is added in amounts from 0.1 to 5 pounds per ton of pulp.

The compositions of the invention may be added to the aqueous system to be controlled in neat form, or in an aqueous or polar organic solution. Liquid solutions of the active ingredients may contain other components such as dispersants and the like. For example, polyoxyalkylene adducts of long chain aliphatic amines or alcohols may be suitably employed as dispersants. A typical compound of this type is known and trade-marked as "Sterox AJ". The biocides used may also be added separately without departing from the spirit of the invention.

If desired, chemical briquette adsorbents such as soda ash, dextrine and the like may be prepared in conjunction with the active materials so that solid materials are produced for direct feeding into the aqueous system with conventional briquette feeding equipment.

EVALUATION OF INVENTION

In order to determine the efficacy of the invention for treating various types of industrial process waters under a wide variety of conditions, and particularly to demonstrate the synergistic effects of the compositions of the invention, the following test method was used. This test method correlated with conditions existing in many industrial process systems where microbiological problems occur. This test method is set forth in detail below:

The culture medium used consisted of 24 grams of dextrose, 1 gram of "Basaminbact", added to one liter of Chicago tap water and sterilized by autoclaving under 15 pounds of pressure for 15 minutes. The final pH of the autoclaved medium was 6.8 ±0.1. An appropriate amount of 18 to 24-hour nutrient broth culture of *A. aerogenes* was mixed with 200 ml. of the culture medium immediately before starting the tests, to give an inoculated culture medium having one million organisms per ml. of medium. This inoculated culture medium was placed in each of a series of fermentation tubes with caps which contained the appropriate concentration of test chemical to give a final volume of test chemical and culture medium of 20 ml. in each tube. For this purpose, the maximum volume of chemical introduced should be 0.5 per tube to avoid chemical-solvent interference. Many solvent carriers of active materials are themselves somewhat effective, and efficient comparative testing requires that only small amounts of these solvents be introduced into the culture medium. The chemical and the inoculated medium were mixed gently. Two control tests were also run, one in which the chemical was omitted, and the second in the absence of inoculum. In mixing, tubes were inverted in the gas inhibition study so as to fill the gas detection vials. Inhibition ranges for *A. aerogenes* were determined by noting the presence or absence of gas production in the gas vials after 18 hours. These ranges were recorded for the synergistic combinations of the inventions and respective components of each combination to demonstrate that the biocidal activities of these combinations were greater than the algebraic sum of the individual effects of the components.

In addition to the 18 hour inhibition test, microbiological activity of certain combinations of the invention were compared to the additive effects of their individual components with regard to 18 hour killing ranges. As indicated in the above test method, an appropriate amount of 18 to 24-hour nutrient broth culture of *A. aerogenes* was mixed with 200 ml. of culture medium so as to give an inoculated culture medium having one million organisms per milliliter of culture medium. This inoculated culture medium was then added to tubes containing appropriate amounts of test chemicals, the total final volume of test chemical and culture medium being 20 milliliters in each tube, the maximum allowable amount of test chemical-solvent interference. The inoculated media and test chemical were then mixed gently, and tubes inverted to fill the gas detection vials. At the end of 18 hours contact with the test chemicals, portions of the liquid in the test were diluted 1000-fold to stop the chemical action. The diluted samples were then cultured into sterile culture tubes, incubated for 48–72 hours at 30°C. and examined for growth. Results of these tests then indicate the 18-hour killing ranges.

Using the above-described inhibition test method, several typical compositions of the invention were prepared and their activity determined. Likewise, activities of the individual components of these compositions were also tested. Results are reported as parts of chemical treating agent necessary to effectively inhibit 1,000,000 organisms. These results are set forth in Table II below:

TABLE II

18-Hour Broth Tube Inhibition Test Results

| Composition | | Inhibition Results (ppm) |
|---|---|---|
| I. | 5% Methylenebisthiocyanate in hydrocarbon solvent | 10–25 |
| III. | 100% 2,4,5-trichlorophenol | 12 |

Weight Ratios Based on Active Ingredients

| Composition Mix | Weight Ratio of Methylenebisthiocyanate to Active Agent | Inhibition Results (ppm) |
|---|---|---|
| I. + III. | 1:0.5 | 2.5–5 |

As can readily be seen by inspection of the above table, the compositions of the invention demonstrate synergistic microbiological activity, and show surprisingly greater activity than the algebraic sum of the individual ingredients which make up the respective compositions.

Table III below sets forth kill results in accordance with the test procedure outlined above. Again, the compositions of the invention demonstrated unexpected synergistic activity compared to the additive effect of their respective components.

TABLE III

18-Hour Broth Tube Kill Test Results

| Composition | Kill Results (ppm) |
|---|---|
| I. | 25 |
| III. | 37 |

Weight Ratios Based on Active Ingredients

| Composition Mix | Weight Ratio of Methylenebisthiocyanate to Active Agent | Inhibition Results (ppm) |
|---|---|---|
| I. + III. | 1:0.8 | 10–25 |

In another test, the compositions of the invention were specially evaluated for their activity in inhibiting the growth and reproduction of bacteria and fungi which create slime. Specifically, the test apparatus was arranged to simulate an industrial cooling tower. This apparatus consisted essentially of a 5-gallon jar containing a series of wooden slats or test plates arranged in such a manner so that each alternate slat would lie directly under the slat above, such as is the situation found in the fill section of a cooling tower. At the start of the test, 10 liters of tap water are put in the jar, nutrient added and the water media allowed to recirculate. As the water recirculates, it strikes the top deck of the ladder and then runs down through the holes in the top deck and over the slats in the same manner as water flow occurs in a typical cooling tower. Cultures of slime-forming organisms are inoculated into the system and the recirculators allowed to run for 96 hours, during which time a heavy slime develops. Chemicals which are to be evaluated are put into the bacterial recirculators at zero hours and slimicide activity determined by ability to prevent slime deposition on the wooden slats or test plates over a period of two days. An initial check is made after 24 hours duration.

Table IV below shows the results of this test in evaluating the compositions of the invention. Again, it is readily apparent that the claimed composition shows synergistic activity in controlling slime formation by inhibiting growth and reproduction of bacteria fungi, etc., causing slime appearance.

TABLE IV

| Composition | ppm Chemical | Slime Control 24 Hrs. | 48 Hrs. |
|---|---|---|---|
| I. | 0.5 | Excellent | None |
| III. | 5 | None | None |

| Composition | ppm Chemical | Ratio-Active Ingredient | Slime Control 24 Hrs. | 48 hrs. |
|---|---|---|---|---|
| I. | 0.5 | 1:10:10 | Excellent | Good |
| II.* | 5 | | | |
| III. | 5 | | | |
| I. | 0.5 | 1:10:10 | Excellent | Good |
| II.* | 5 | | | |
| III. | 5 | | | |

*17% 1-alkyl ($C_{12}$)-amine-3-amino propane mono acetate in aqueous-alcoholic solution Excellent — No slime formation
Good — Little slime formation
Fair — Moderate slime formation
None — Heavy slime formation It was interesting to note that many well-known microbiocidally active chemicals, greatly differing in molecular structure did not exhibit synergistic activity when combined with methylenebisthiocyanate. Among these, just a few include dinitrochlorobenzenemethyldibromopropionate, 2,3-dichloro -1,4-naphthoquinone and bromoacetoxypropanol. Also, in a bulletin released by American Cyanamid in October, 1963, it was suggested that methylenebisthiocyanate, identified as E. B. 18,903 could be formulated with a variety of corrosion inhibitors, dyes, antifoams and other biocides. Yet it was determined that upon testing that two of the suggested additional biocides, alkyl ($C_{16-18}$) dimethyl benzyl ammonium salt and alkyl ($C_{12-18}$) trimethyl ammonium salt, did not exhibit any trace of synergism in combination with methylenebisthiocyanate. In fact, the former material actually exhibited an antagonistic effect toward methylenebisthiocyanate; that is, the combination of the two showed less than an additive effect.

The above tables show that representative compositions of the invention possess excellent activity in inhibiting the growth of as well as in killing bacteria. The A. aerogenes bacteria are particularly prevalent in industrial process water systems and especially are prone to occur and accumulate in aqueous paper pulp being processed into paper articles and as well as in cooling tower systems. The compositions of the invention also show particularly excellent synergistic activity in inhibiting the growth and reproduction of other bacterial and fungal organisms.

While the compositions of the invention find special use in paper mill water systems and industrial cooling towers, they may likewise be effectively employed in reducing and/or inhibiting growth of microorganisms in air conditioning equipment, internal combustion engines, the secondary recovery of petroleum in the process known as waterflooding, water wells and similarly related industrial flood systems.

It is apparent that many modifications and improvements may be made without departiing from the scope and invention which is not to be limited other than as recited in the appended claims.

The expressions "microbiocidal agent" or "microbiocide" as used herein are meant to designate chemical substances which have killing and/or inhibiting action on such organisms as, for example, bacteria, fungi, algae, protozoa, and the like.

The invention is hereby claimed as follows:

1. An antifungal and antibacterial composition which consists essentially of methylenebisthiocyanate and 2,4,5-trichlorophenol combined in a weight ratio of from 1:0.1 to 1:20.

2. The composition of claim 1 where the methylenebisthiocyanate and 2,4,5-trichlorophenol are combined in a weight ratio of from 1:05 to 1:10.

3. A method for inhibiting the growth and reproduction of fungi or bacteria in water systems which comprises the step of treating said system with an antifungal and antibacterial composition consisting essentially of methylenebisthiocyanate and 2,4,5-trichlorophenol combined in a weight ratio of from 1:0.1 to 1:20.

4. The method of claim 3 where the methylenebisthiocyanate and 2,4,5-trichlorophenol are combined in a weight ratio of from 1:0.5 to 1:10.

5. An antifungal and antibacterial composition comprising from about 0.1 to about 20 parts by weight of 2,4,5-trichlorophenol and about one part by weight of methylenebisthiocyanate.

6. The antifungal and antibacterial composition of claim 5 wherein the 2, 4, 5- trichlorophenol is present in an amount of about 10 parts by weight of the methylenebisthiocyanate.

7. The method of inhibiting growth of fungi or bacteria comprising applying to a substance which is subject to attack by fungi and bacteria a fungicidally or bactericidally effective amount of the composition of claim 5.

8. The method of inhibiting growth of fungi or bacteria comprising applying to a substance which is subject to attacks by fungi and bacteria a fungicidally or bactericidally effective amount of the composition of claim 6.

9. An antifungal and antibacterial composition comprising from about 0.5 to about 20 parts by weight of 2,4 5-trichlorophenol and about one part by weight of methylenebisthiocyanate.

10. The method of inhibiting growth of fungi or bacteria comprising applying to a substance which is subject to attacks by fungi and bacteria a fungicidally or bactericidally effective amount of the composition of claim 9.

* * * * *